United States Patent [19]
Blasdell et al.

[11] Patent Number: 5,419,317
[45] Date of Patent: * May 30, 1995

[54] INHALATION APPARATUS

[75] Inventors: Richard J. Blasdell, Phoenix; Raymond L. Blasdell, Litchfield Park, both of Ariz.

[73] Assignee: Accutron, Phoenix, Ariz.

[ * ] Notice: The portion of the term of this patent subsequent to May 17, 2011 has been disclaimed.

[21] Appl. No.: 222,586

[22] Filed: Apr. 1, 1994

Related U.S. Application Data

[63] Continuation of Ser. No. 878,838, May 4, 1992, Pat. No. 5,311,862, which is a continuation-in-part of Ser. No. 270,003, Nov. 14, 1988, Pat. No. 5,109,839.

[51] Int. Cl.⁶ .................................................. A62B 7/00
[52] U.S. Cl. ............................... 128/205.19; 128/910
[58] Field of Search ....................... 128/203.12, 205.25, 128/205.19, 910

[56] References Cited

U.S. PATENT DOCUMENTS

| | | | |
|---|---|---|---|
| 2,868,198 | 1/1959 | Brooke | 128/205.24 |
| 4,151,843 | 5/1979 | Brekke et al. | 128/205.25 |
| 4,219,020 | 8/1980 | Czajka | 128/910 |
| 4,248,218 | 2/1981 | Fischer | 128/910 |
| 4,265,239 | 5/1981 | Fischer, Jr. et al. | 128/910 |
| 4,702,241 | 10/1987 | Gravenstein et al. | 128/205.19 |
| 4,770,169 | 9/1988 | Schmoegner et al. | 128/910 |
| 5,033,464 | 7/1991 | Delcastilho | 128/205.19 |
| 5,109,839 | 5/1992 | Blasdell et al. | 128/205.25 |
| 5,311,862 | 5/1994 | Blasdell et al. | 128/205.25 |

Primary Examiner—Edgar S. Burr
Assistant Examiner—Aaron J. Lewis
Attorney, Agent, or Firm—Parsons & Associates; Don J. Flickinger; Robert A. Parsons

[57] ABSTRACT

A face mask includes a cup-shaped body for enclosing an external respiratory organ, such as the nose, of a patient. Flow of a respirable gas into the body and exhaust of expired gas from the body are unidirectional controlled by respiration check valves. A plurality of detachably securable and interchangeable accessory devices adapt the mask for use with selected prior art scavenging devices.

6 Claims, 3 Drawing Sheets

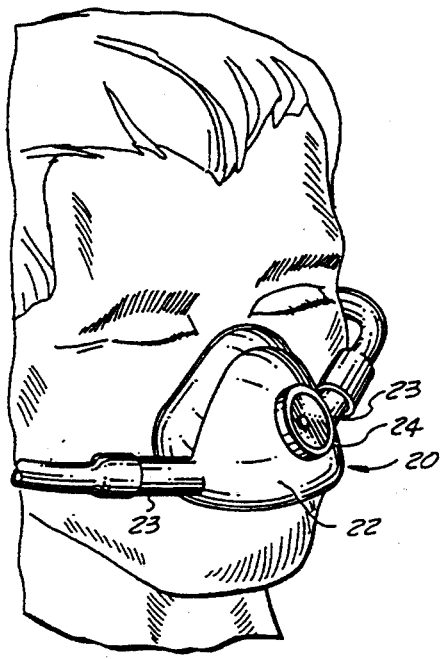
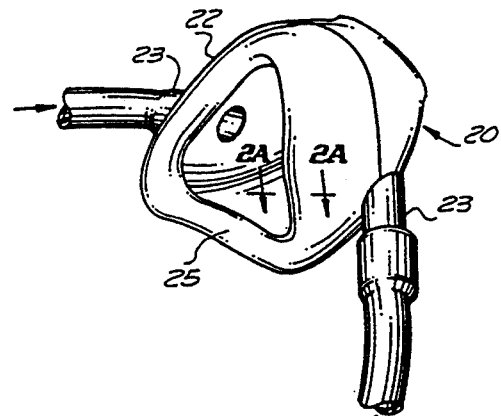
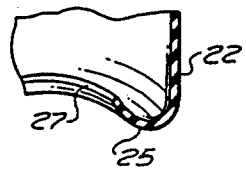
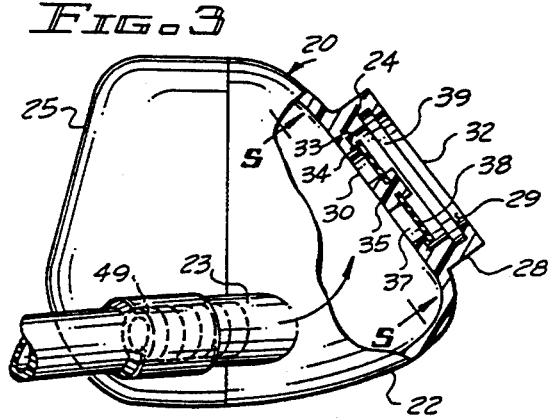
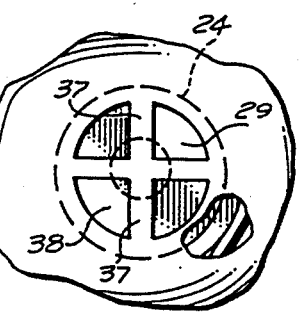
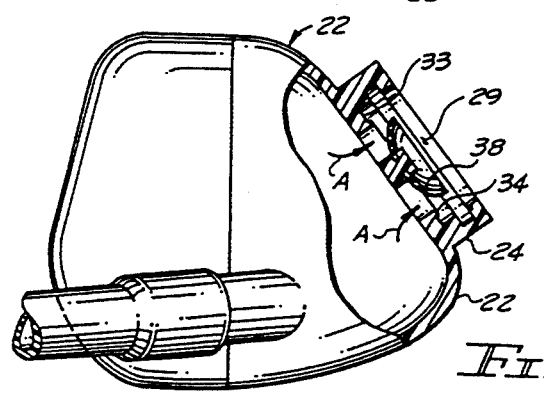
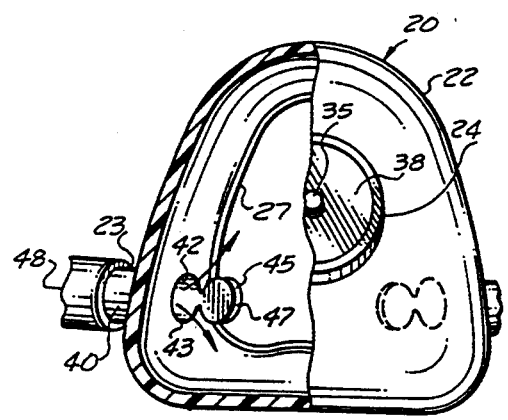

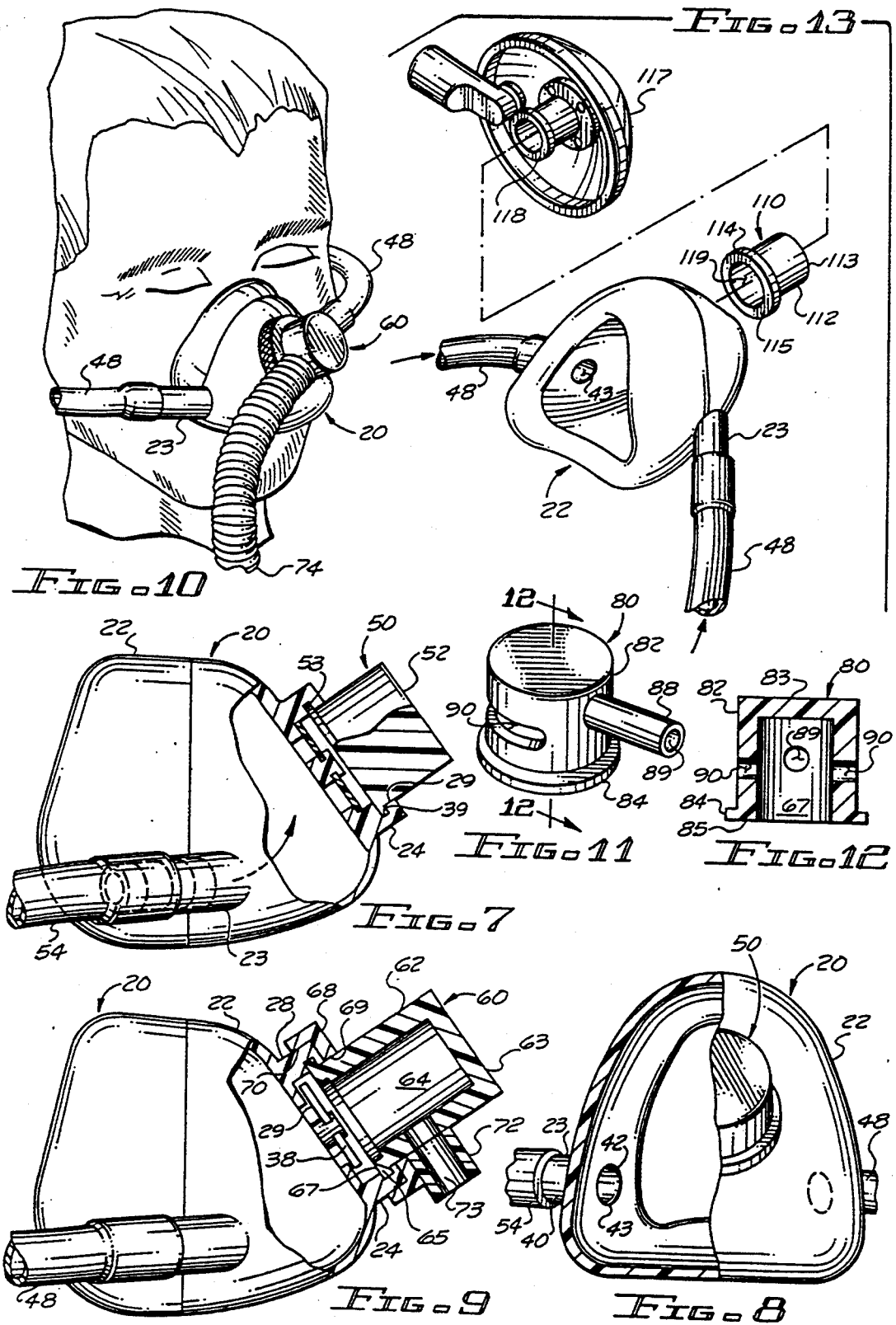

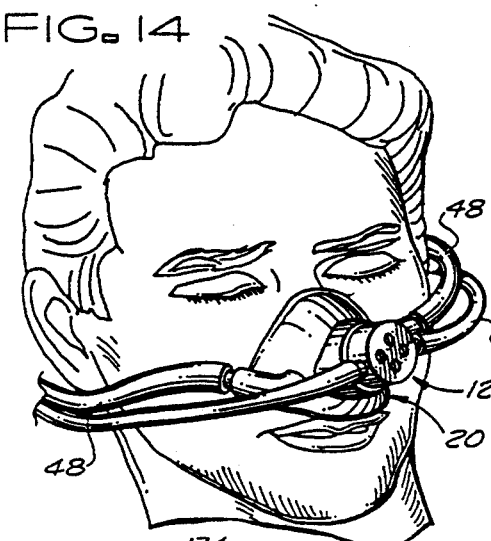
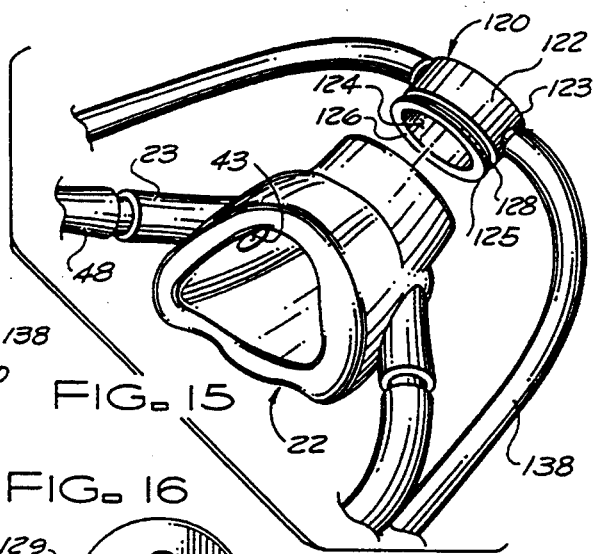
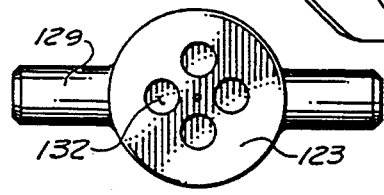
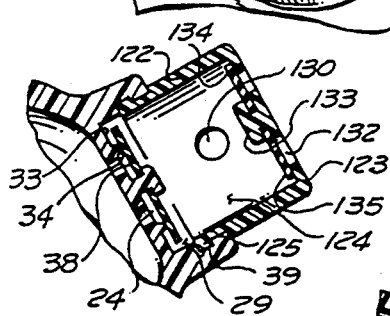
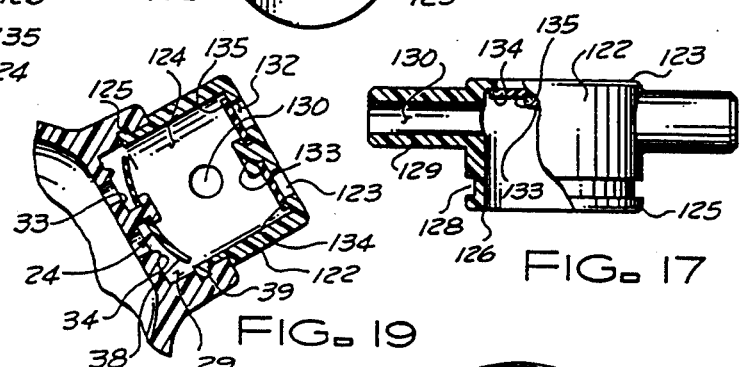
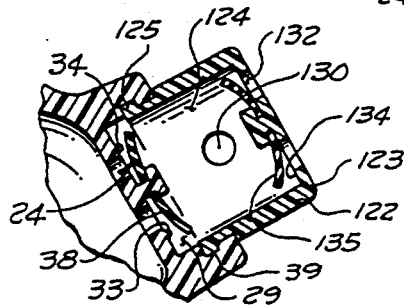
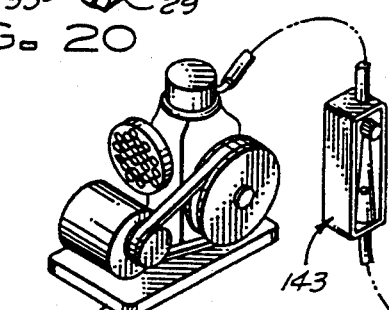
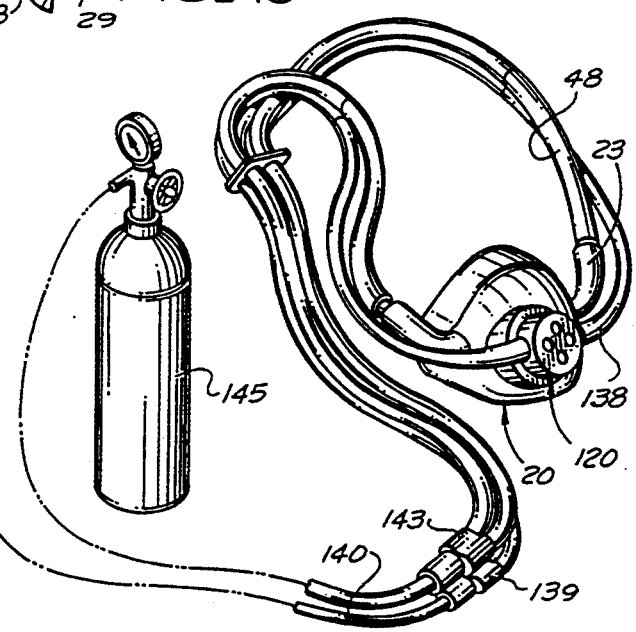

INHALATION APPARATUS

This application is a continuation, of application Ser. No. 07/878,838, filed 4 May, 1992 now U.S. Pat. No. 5,311,862, which application is a continuation-in-part of prior application Ser. No. 07/270,003, filed Nov. 14, 1988 now U.S. Pat. No. 5,109,839.

BACKGROUND OF THE INVENTION

1. Field of the Invention

This invention relates to respiratory or inhalation systems.

More particularly, the present invention relates to apparatus for administering a respirable gas to a patient.

In a further and more specific aspect, the instant invention concerns improvements in face masks and accessories of the type especially adapted for use in an inhalation system.

2. Prior Art

Inhalation or respiratory systems for administering respirable gas to an individual are well-known. Especially recognized are apparatus employed in the medical and dental arts for dispensing anesthetic and analgesic gases to a patient. Exemplary familiar gases are oxygen and nitrous oxide.

Typically, inhalation systems include a source of a selected pressurized gas and means to deliver the gas to the external respiratory organs of the patient. A breathing device, such as a mask, is fitted to the face of the patient to embrace the nose and/or the mouth. The source, which may be either portable or fixed, usually includes a flow regulator. A delivery conduit, generally in the form of a flexible hose, communicates between the source and the breathing device. Optionally, the system may include scavenging apparatus comprising a return conduit extending from the breathing device to a source of vacuum.

The prior art has devised an array of personal breathing devices in numerous structural configurations. More commonly referred to as inhalation masks or face masks, the devices serve a variety of specific functions. Known, for example, are masks which extend over the mouth and the nose of the patient while others receive only the nose. Commonly, masks include a fitting for attachment of a gas delivery conduit. Infrequently, an exhalation valve is incorporated into a mask to prevent the entrance of ambient air.

Recently, there has arisen a concern over expired gas. A solution purposed by the prior art is in the form of a vacuum scavenger valve attachment for retrofit to certain pre-existing inhalation masks. To accommodate the attachment, the mask must include an exhalation valve body of exacting configuration, which must be removed. In addition to the wastefulness of the discarded valve body and the inconvenience of effecting the conversion, the attachment is exceedingly complex having an encumbered chamber and valving assembly.

An additional problem with vacuum scavengers is finding the correct balance between vacuum pressure and a patients respiration. In some instances, if the vacuum is to strong, it may suck the breath right out of a patient. In other instances the individual may struggle to inhale against a vacuum which has opened a valve and is removing unexpired gases. This is usually elliviated by reducing the vacuum pressure. However, sometimes the balance is delicate, in which case any change in the patients breathing, such as becoming slower, or less forceful, may result in the vacuum becoming to strong. In the present art, this would require readjusting the vacuum pressure, which would be inconvenient in the middle of a procedure.

Other inadequacies of the prior art are equally disconcerting. Masks with metallic components, for example, are not compatible with the use of X-ray equipment. Ever present is the concern over proper fit and sealing engagement with the facial area while concurrently ensuring patient comfort. Further, not heretofore satisfactorily addressed, is the rise in the anxiety level of an already distressed patient as a result of having the breathing facilities encapsulated and the contemplation of inhaling a foreign substance.

It would be highly advantageous, therefore, to remedy the foregoing and other deficiencies inherent in the prior art.

Accordingly, it is an object of this invention to provide improvements in inhalation masks.

Another object of the invention is the provision of a face mask which is especially adapted for use in combination with conventional medical and dental inhalation systems.

And another object of the invention is to provide a mask which is readily usable with pre-existing, commercially available scavenging apparatus.

Yet another object of the instant invention is the provision of a mask having integral valving for controlling the flow of gases therethrough.

Still another object of the invention is to provide ameliorated means for sealing mask to the facial area of a user.

Yet still another object of this invention is the provision of a mask which readily conforms to the face of the user and is exceedingly comfortable to wear.

A further object of the immediate invention is to provide a face mask which is compatible with X-ray technology.

And a further object of the invention is the provision of improvements for alleviating patient anxiety or apprehension.

Yet a further object of the present invention is to provide an inhalation mask which includes an adapter attachment which would allow various different vacuum scavenging apparatus to be attached to the mask.

And yet a further object of the invention is the provision of a mask, according to the foregoing, which is sufficiently inexpensive to manufacture to be considered disposable.

Another object of the invention is to provide a mask with a vacuum scavenger apparatus.

Still another object of the invention is to provide a vacuum scavenger apparatus having a relief valve to prevent unintentional removal of unexpired gases.

SUMMARY OF THE INVENTION

Briefly, to achieve the desired objects of the instant invention in accordance with a preferred embodiment thereof, first provided is an inhalation mask having a generally cup-shaped body receivable against the facial area of an individual and for enclosing a respiratory organ. An inhalation valve assembly and an exhalation valve assembly are carried by the body. The inhalation valve assembly includes an inlet port for receiving respirable gas from a source thereof and a check valve for unidirectional flow of the respirable gas into the body. The exhalation valve includes an inlet port, a check valve for unidirectional flow of expired gas through the port and attachment receiving means for receiving the attachment means of an accessory device.

In accordance with a more specific embodiment of the invention, the inlet check valve includes an endless valve seat and a flapper member movable between an open position and a closed position. The exhalation valve assembly includes a bore and the check valve includes an annular valve seat formed in the bore and a valve disc normally residing in closed position against the annular valve seat. The disc is resiliently deformable to lift from the seat in response to a predetermined positive pressure within the bore. The outlet check valve and the attachment receiving means are coaxial with the longitudinal axis of the bore with the attachment means residing outboard of the valve.

In yet a further embodiment, the body, which is preferably fabricated of a thermoplastic elastomer, terminates with a deformable endless peripheral edge which is sufficiently pliant for substantial sealing engagement against the facial area of the individual. Preferably, the peripheral edge is accurately inturned in cross section.

Further provided by the present invention is a plurality of accessory devices which adapt the inhalation mask for use with a plurality of prior art scavenging devices. Each accessory device includes a body having attachment means which are engagable with the attachment receiving means of the inhalation mask. In accordance with a specific embodiment thereof, the body of the accessory device is hollow having a chamber therein which receives expired gas from the exhalation valve assembly and attachment means for connection with the scavenging device to receive the expired gas from the chamber. In an alternate embodiment, the body of the accessory device functions as a plug for effectively closing the exhalation valve assembly. In a further embodiment, the accessory device includes a relief valve to prevent the unintentional removal of unexpired gases.

BRIEF DESCRIPTION OF THE DRAWINGS

The foregoing and further and more specific objects and advantages of the instant invention will become readily apparent to those skilled in the art from the following detailed description of preferred embodiment thereof taken in conjunction with the drawings in which:

FIG. 1 is a perspective view of an inhalation mask constructed in accordance of the teachings of the instant invention as it would appear in use;

FIG. 2 is a rear perspective view of the inhalation mask of FIG. 1;

FIG. 2A is an enlarged fragmentary horizontal sectional view taken along the line 2A—2A of FIG. 2;

FIG. 3 is an enlarged side elevation view of the inhalation mask of FIG. 1 having a portion thereof broken away to further illustrate the exhalation valve assembly as shown in the normal or closed position;

FIG. 4 is a view generally corresponding to the view of FIG. 3 and particularly illustrating the exhalation valve assembly as it would appear in the open or exhaust position;

FIG. 5 is a fragmentary vertical sectional view taken along line 5—5 of FIG. 3 and having a portion thereof broken away for purposes of illustration;

FIG. 6 is a front elevation view of the mask of FIG. 1, the left hand portion thereof being broken away for purposes of illustrating the inhalation valve assembly;

FIG. 7 is a view generally corresponding to the view of FIG. 3 and illustrating an accessory device of the instant invention attached thereto;

FIG. 8 is a front elevation view of the inhalation mask and accessory device seen in FIG. 7, the left hand portion thereof being broken away to show a companion modification to the inhalation valve assembly;

FIG. 9 is a view generally corresponding the view of FIG. 7 and illustrating an alternate accessory device secured to the inhalation mask;

FIG. 10 is a perspective view of the inhalation mask and accessory device of FIG. 9 as it would appear in use;

FIG. 11 is a perspective view of yet another accessory device usable in combination with the inhalation mask of the instant invention;

FIG. 12 is a vertical sectional view taken along the line 12 of FIG. 11;

FIG. 13 is an exploded perspective view, generally corresponding to the view of FIG. 2, and showing yet a still further accessory device usable in combination with the inhalation mask of the instant invention;

FIG. 14 is a perspective view of an inhalation mask and vacuum scavenger as it would appear in use;

FIG. 15 is an exploded perspective view, generally corresponding to the view in FIG. 2, and showing the attachment of the adapter and vacuum relief valve;

FIG. 16 is a top view of the vacuum relief valve adaptor;

FIG. 17 is partial cross sectional side view of the vacuum relief valve adaptor;

FIG. 18 is a cross-sectional side view of the vacuum relief valve adaptor coupled to the mask;

FIG. 19 is substantially the same view as FIG. 18, showing the exhaust valve open;

FIG. 20 is substantially the same view as FIG. 18 showing the exhaust valve and the relief valve open; and FIG. 21 is a perspective view of the mask with the vacuum scavenger apparatus attached.

DESCRIPTION OF THE PREFERRED EMBODIMENT

Turning now to the drawings in which like reference characters indicated corresponding elements throughout the several views, attention is restricted to FIG. 1, which shows an inhalation mask embodying the teachings of the instant invention and generally designated by the reference character 20. Mask 20 includes body 22, inhalation valve assembly 23 and exhalation valve assembly 24. Preferably, two inhalation valve assemblies 23 are included, one extending from either lateral side of body 22. The single exhalation valve assembly 24 is located at a frontal midpoint.

Body 22, as seen with additional reference to FIG. 2, is generally cup-shaped, terminating with rearwardly directed peripheral edge 25. Edge 25, as seen in cross section in FIG. 2A, comprises a terminal portion of body 22, which is inturned to form a semi-cylindrical bead having inwardly directed free edge 27. Body 22 is sized to receive at least one of the external respiratory organs, such as the nose, of an individual as specifically illustrated in FIG. 1. Edge 25 is contoured to be received against the facial area surrounding the nose.

Preferably, body 22 is molded of a flexible elastic material, such as the thermoplastic elastomer distributed under the trademark Kraton ®. Being of reduced thickness, the terminal portion forming peripheral edge 25 is readily deformable to be pliantly received against the facial area in sealing engagement therewith.

In accordance with the immediately preferred embodiment of the invention, exhalation valve 24 includes integrally formed exhalation valve body 28 projecting outwardly from body 22. Bore 29 extending through tubular member 28 and body 22 and functioning as an outlet port, terminates with inlet end 30 and outlet end 32. Outwardly directed annular valve seat 33, having annular ride 34 projecting therefrom, is formed in bore 29 proximate inlet end 30. Post 35 is coaxially held within bore 29 by a spider-like arrangement of support members 37 which extend radially between post 35 and the sidewalls of bore 29 intermediate valve seat 33 and inlet end 30. Valve disc 38, preferably a relatively thin resiliently deformable member which may also be fabricated of a thermoplastic material, is carried by post 35. Annular groove 39, functioning as an attachment receiving means as will be described presently, is formed coaxially into bore 29 proximate outlet end 32.

Normally, valve disc 38 resides against valve seat 33 in the closed position as seen in FIG. 3. In response to inhalation of the individual, valve disc 38 is drawn with greater force into sealing engagement with annular ridge 34. In response to exhalation of the individual, valve disc 38 deflects from valve seat 33 for exhaust of expired gases in the direction of arrowed lines A as seen in FIG. 4. Accordingly, it is seen that disc 38 and valve seat 34 function as an outlet check valve for unidirectional flow of expired gas through outlet port 29.

Each inhalation valve 23 includes an inhalation valve body 40 projecting from body 22 and having a bore therethrough defined by cylindrical sidewall 42. Inhalation valve body 40 projects angularly rearward from body 22. Accordingly, the outlet end 43 of bore 42 is generally eliptical, being askew to the longitudinal axis of bore 42. The terminal portion of bore 42 adjacent end 43 functions as a valve seat for flapper member 45 which is hingedly affixed to body 22. Inhalation valve body 40 and flapper member 45, analogous to post 35 and support members 37, are integrally formed with body 22. The peripheral edge 47 of flapper member 45 is shaped to be matingly received within the previously described valve seat.

A respirable gas is transmitted to mask 20 from a source thereof through a delivery conduit, such as hose 48. As will be appreciated by those skilled in the art, respirable gases for anesthetic and analgesic purposes, such as oxygen and nitrous oxide, are commonly employed in the medical and dental arts. As such, a pressurized supply of a selected gas is readily available in medical and dental facilities. Delivery conduit 48 may be directly connected to inhalation valve body 40. Alternately, there is provided a connecting nipple 49 as particularly seen in FIG. 3. Nipple 49, a relatively rigid tubular member, is partially inserted into the inlet end of inhalation valve body 40 and partially into the outlet end of delivery conduit 48.

It should also be noted that mask 20 is molded in a single piece from a homogeneous elastomeric material. Therefore, for purpose of this application, when the term integral is used to refer to an element, such as inhalation valve body 40 or exhalation valve body 28, that element is molded into a single continuous structure of homogeneous material with body 22 to form mask 20.

Expired gas emitted from exhalation valve 24, when mask 20 is used as seen in FIG. 1, is delivered to the ambient atmosphere. Under certain circumstances it is desirable that the expired gas be captured for remote disposal. For this purpose, the prior art has provided various scavenging devices which cooperate with a source of vacuum generally available in medical and dental facilities. Previously described mask 20 comprises a component of an inhalation system which further includes various accessory devices provided by the instant invention. Mask 20 and each selected accessory device provide an inhalation apparatus which is adapted for use with a selected commercially available scavenging apparatus.

Referring now to FIG. 7, there is seen an accessory device generally designated by the reference character 50 having cylindrical body 52 and outwardly directed annular flange 53. The terminal portion of body 52 adjacent flange 53 is matingly receivable within bore 29 of exhalation valve 24. Flange 53 is matingly receivable within annular groove 39. Thus, it is seen that the terminal portion of body 52 and flange 53 function as attachment means for accessory device 50, which is receivable within the attachment receiving means of valve assembly 24. Accessory device 50 functions as an adapter plug to sealingly close outlet port 39 and render exhalation valve assembly 24 inoperative.

Further, in accordance with the immediate embodiment of the invention, the flapper member associated with one of the inhalation valve assemblies 23 is removed. For purposes of illustration, the left hand flapper valve, as mask 20 is viewed in FIG. 8, has been removed. An exhaust conduit 54 associated with a selected prior art scavenging system is secured to the respective inhalation valve body 40. Delivery conduit 48 is attached to the other inhalation valve assembly 23 with flapper member 45 intact as previously described.

Attention is now directed to FIGS. 9 and 10 which illustrate an alternate accessory device generally designated by the reference character 60, including hollow cylindrical body 62 closed at the outboard end by endwall 63 to form chamber 64 therein. Annular flange 65 encircles body 62 proximate the inboard end 66 thereof. Analogous to the previously described embodiment, flange 65 and the exterior portion of cylindrical body 62 adjacent flange 67 function as attachment means to be received by the attachment receiving means of the exhalation valve assembly 24 of mask 20. The attachment is further reinforced by locking ring 68 having bore 69 therethrough which is rotatably and slidably received upon body 62 and internal surface 70 which frictionally engages the exterior surface of tubular member 28. Nipple 72 projects radially from body 62. Opening 73, functioning as an exhaust port, extends through nipple 72 and the sidewall of body 62 to communicate with chamber 64.

Accessory device 60 serves to adapt mask 20 for use with another known prior art scavenging device as represented by the flexible conduit 74 seen in FIG. 10. With accessory device 60 attached, the check valve associated with exhalation valve assembly 24 remains fully operational. Accessory device 60 functions as a manifold for receiving expired gases from body 22 and transferring said gases to flexible conduit 74. Delivery conduits 48 are connected with the inhalation valve assemblies 23 as previously described.

Another alternate accessory device, generally designated by the reference character 80 and usable in combination with the previously described mask 20, is seen with reference to FIGS. 11 and 12. The immediate embodiment includes hollow cylindrical body 82 closed at the outboard end by endwall 83 and having outwardly directed annular flange 84 proximate the inboard end 85. Chamber 67 resides within body 82. Nipple 88 projects from body 82 and includes bore 89 extending therethrough and communicating with chamber 67. Vent openings 90 project through body 82 for communication between chamber 67 and the ambient environment. Accessory device 80 is connected with the exhalation valve assembly 24 of mask 20 as previously described and functions as an adapter whereby the inhalation apparatus is usable with yet another commercially available scavenging system.

Yet another accessory device, generally designated by the reference character 110 is illustrated in FIG. 13. The accessory device 110 includes tubular body 112 having an open outboard end 113 and an outwardly projecting annular flange 114 proximate inboard end 115. Accessory device 110, which is securable to mask 22 as previously described, functions as an adapter for attachment of a scavenging valve assembly of the prior art designated by the reference character 117. Tubular connection member 118 associated with valve attachment 117 is frictionally received with the bore 119 of accessory device 110.

Attention is now directed to FIGS. 14 and 15 which illustrate an accessory device generally designated 120, attached to mask 20. Accessory device 120 includes a hollow cylindrical body 122 closed at the outboard end by endwall 123 to form a chamber 124 therein. An annular flange 125 encircles body 122 proximate the inboard end 126 thereof. The terminal portion of body 122 adjacent flange 125 has an annular groove 128 therein, and is matingly receivable within bore 29 of exhalation valve 24. Flange 125 is matingly receivable within annular groove 39, while the terminal portion of exhalation valve 24 is matingly receivable within groove 128.

Referring now to FIGS. 16 and 17, nipples 129 project from body 122, and include bores 130 extending therethrough and communicating with chamber 124. Vent openings 132 project through endwall 123 for communication between chamber 124 and the ambient environment. With further reference to FIG. 18, a central post 133 extends coaxially from endwall 123 into chamber 124. Inwardly directed annular valve seat 134 is formed in chamber 124 proximate endwall 123. A valve disc 135 is carried by post 133.

Normally, valve disc 135 resides against valve seat 134 in the closed position as seen in FIG. 18. This closes vent openings 132 preventing communication between chamber 124 and the ambient environment. Valve disc 38 of exhalation valve 24 also resides against valve seat 33 in the closed position. In response to inhalation of the individual, valve disc 38 is drawn with greater force into sealing engagement with annular ridge 34. In response to exhalation of the individual, valve disc 38 deflects from valve seat 33 for exhaust of expired gases into chamber 124 as illustrated in FIG. 19. During exhalation, the ingress of expired gases into chamber 124 forces valve disc 125 into sealing engagement with valve seat 124, sealing chamber 124 from the ambient environment. Scavenging conduits 138 then remove the expired gases from chamber 124. This is the optimal situation, when the vacuum pressure is properly balanced with an individuals respiration. However, if the vacuum generated is to strong, during inhalation valve disc 38 would deflect from valve seat 33 causing the withdrawal of gases from mask 20 before they were inhaled if relief valve was not present. However, accessory device 120 prevents this as illustrated in FIG. 20. If the vacuum pressure is to strong, instead of deflecting valve disc 38 from valve seat 33 valve disc 135 is deflected from valve seat 134. This allows the individual to properly inhale the gases while the vacuum withdraws air from the ambient environment through vent openings 132. Upon exhalation by the individual, valve disc 38 is deflected from valve seat 33 with expired gases being exhausted into chamber 124 forcing valve disc 135 into sealing engagement with valve seat 134.

Referring now to FIG. 21, accessory device 120 is illustrated attached to mask 20, and a vacuum scavenger apparatus generally designated 136. In this embodiment, a pair of flexible hoses 138 extend from nipples 129 of accessory device 120, to a two into one adapter 139. A single hose 140 extends from adapter 139 to a vacuum source 142. An adjustable gauge 143 is incorporated into vacuum hose 140 to allow the vacuum supplied to accessory device 120 to be adjusted. Delivery conduits 48 extend from inhalation valve assemblies 23 to a two into one delivery adapter 143. A single delivery conduit extends from adapter 143 to a gas source 145.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described and disclosed a present invention and alternate embodiments thereof in such clear and concise terms as to enable those skilled in the art to understand and practice the same, the invention claimed is:

1. A vacuum scavenger device for removing expired gases from a breathing mask having an exhalation valve and for preventing unintentional removal of unexpired gases, said vacuum scavenger device comprising:
   a) an adapter removably attachable to said exhalation valve;
   b) a vacuum conduit coupling a vacuum source to said adapter; and
   c) a relief valve formed in said adapter selectively coupling said vacuum source to an outside atmosphere for relieving excess negative pressure generated by said vacuum source.

2. A vacuum scavenger device as claimed in claim 1 wherein said adapter further comprises:
   a) a body having sidewalls defining a chamber, a first inlet form in a first end and a second inlet formed in a second end closed by said relief valve;
   b) attachment means for coupling said adapter to said exhalation valve assembly; and
   c) a conduit coupling extending from said sidewalls, having a bore extending therethrough and into said chamber.

3. A vacuum scavenger device as claimed in claim 2 wherein said relief valve further comprises:
   a) a valve seat formed in said chamber, coaxial with said second inlet and directed towards said first inlet;
   b) a post supported within said chamber, coaxial with said valve seat; and
   c) a valve disc mounted on said post, said valve disc normally residing in a closed position against said valve seat, and movable from said valve seat into an open position in response to a predetermined negative pressure within said chamber.

4. A vacuum scavenger device as claimed in claim 1 further comprising an adjustable gauge coupled to said vacuum conduit between said adapter and said vacuum source.

5. An adapter for coupling a vacuum scavenger device to a breathing mask having an exhalation valve and for preventing unintentional removal of unexpired gases, said adapter comprising:
   a) a body having sidewalls defining a chamber, a first inlet formed in a first end and a second inlet formed in a second end closed by a relief valve selectively coupling said vacuum scavenger to an outside atmosphere for relieving excess negative pressure generated by said vacuum scavenger;
   b) attachment means for coupling said adapter to said exhalation valve; and
   c) a conduit coupling extending from said sidewalls, having a bore extending therethrough and into said chamber.

6. An adapter as claimed in claim 5 wherein said relief valve further comprises:
   a) a valve seat formed in aid chamber, coaxial with said second inlet and directed towards said first inlet;
   b) a post supported within said chamber, coaxial with said valve seat; and
   c) a valve disc mounted on said post, said valve disc normally residing in a closed position against said valve seat, and movable from said valve seat into an open position in response to a predetermined negative pressure within said chamber.

* * * * *